United States Patent
Dombro et al.

(10) Patent No.: US 7,426,104 B2
(45) Date of Patent: Sep. 16, 2008

(54) METHOD AND APPARATUS FOR INSULATIVE FILM FOR CAPACITOR COMPONENTS

(75) Inventors: Ron Dombro, St. Paul, MN (US); John Longsy Dinh, Maple Grove, MN (US); Gregory J. Sherwood, North Oaks, MN (US); Mark A. Lamberty, Cottage Grove, MN (US); Leonard Goldstein, Shoreview, MN (US); Brian D. Schenk, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 319 days.

(21) Appl. No.: 11/124,792

(22) Filed: May 9, 2005

(65) Prior Publication Data
US 2006/0061938 A1    Mar. 23, 2006

Related U.S. Application Data

(60) Provisional application No. 60/588,905, filed on Jul. 16, 2004.

(51) Int. Cl.
*H01G 9/00* (2006.01)
*H01G 2/10* (2006.01)

(52) U.S. Cl. ................................. 361/503; 361/517
(58) Field of Classification Search ................ 361/503, 361/508, 516–519, 520
See application file for complete search history.

(56) References Cited

U.S. PATENT DOCUMENTS

| | | |
|---|---|---|
| 3,597,276 A | 8/1971 | Jammet |
| 3,659,615 A | 5/1972 | Enger |
| 3,871,921 A | 3/1975 | Beatty et al. |
| 3,982,966 A | 9/1976 | Beatty et al. |
| 4,267,566 A | 5/1981 | Moresi, Jr. |
| 4,286,302 A | 8/1981 | Owens et al. |
| 4,383,011 A | 5/1983 | McClelland et al. |
| 4,385,342 A | 5/1983 | Puppolo et al. |
| 4,931,899 A | 6/1990 | Pruett |
| 4,980,798 A | 12/1990 | Lavene |

(Continued)

FOREIGN PATENT DOCUMENTS

DE    3616991    11/1987

(Continued)

OTHER PUBLICATIONS

Doffing, Brian, et al., "Method and Apparatus for a Capacitor Shell Including Two Mateable Cupped Components", U.S. Appl. No. 11/124,705, filed May 9, 2005, 25 Pages.

(Continued)

*Primary Examiner*—Eric Thomas
(74) *Attorney, Agent, or Firm*—Schwegman, Lundberg & Woessner, P.A.

(57) ABSTRACT

The present subject matter includes an apparatus including a capacitor stack, including at least one substantially planar anode layer arranged in stacked alignment adjacent at least one substantially planar cathode layer, with at least one separator layer disposed therebetween. In this embodiment, the present subject matter includes at least one conformed film at least partially enveloping the capacitor stack in a bound state and adapted to electrically isolate the capacitor stack.

20 Claims, 15 Drawing Sheets

U.S. PATENT DOCUMENTS

| | | | |
|---|---|---|---|
| 5,131,388 | A | 7/1992 | Pless et al. |
| 5,370,663 | A | 12/1994 | Lin |
| 5,371,650 | A | 12/1994 | Lavene |
| 5,439,760 | A | 8/1995 | Howard et al. |
| 5,744,261 | A | 4/1998 | Muffoletto et al. |
| 5,808,857 | A | 9/1998 | Stevens |
| 5,814,082 | A | 9/1998 | Fayram et al. |
| 5,814,090 | A | 9/1998 | Latterell et al. |
| 6,004,692 | A | 12/1999 | Muffoletto et al. |
| 6,040,082 | A | 3/2000 | Haas et al. |
| 6,184,324 | B1 | 2/2001 | Benz et al. |
| 6,225,778 | B1 | 5/2001 | Hayama et al. |
| 6,293,974 | B1 | 9/2001 | Kobatake et al. |
| 6,297,943 | B1 | 10/2001 | Carson |
| 6,321,114 | B1 | 11/2001 | Nutzman et al. |
| 6,388,866 | B1 | 5/2002 | Rorvick et al. |
| 6,423,104 | B1 | 7/2002 | Omori et al. |
| 6,426,861 | B1 | 7/2002 | Munshi |
| 6,467,142 | B1 | 10/2002 | Shirashige et al. |
| 6,493,212 | B1 | 12/2002 | Clarke et al. |
| 6,522,520 | B2 | 2/2003 | Hashizume |
| 6,528,133 | B1 | 3/2003 | Kim et al. |
| 6,556,863 | B1 | 4/2003 | O'Phelan et al. |
| 6,585,152 | B2 | 7/2003 | Farahmandi et al. |
| 6,603,654 | B2 | 8/2003 | Rorvick |
| 6,678,559 | B1 | 1/2004 | Breyen et al. |
| 6,699,265 | B1 | 3/2004 | O'Phelan et al. |
| 6,795,729 | B1 | 9/2004 | Breyen et al. |
| 2002/0071240 | A1 | 6/2002 | Rorvick et al. |
| 2003/0120320 | A1 | 6/2003 | Solom |
| 2003/0204216 | A1 | 10/2003 | Ries et al. |
| 2004/0127952 | A1 | 7/2004 | O'Phelan et al. |
| 2004/0147960 | A1 | 7/2004 | O'Phelan et al. |
| 2004/0147961 | A1 | 7/2004 | O'Phelan et al. |
| 2004/0220627 | A1 | 11/2004 | Crespi et al. |

FOREIGN PATENT DOCUMENTS

| | | |
|---|---|---|
| EP | 0044068 A2 | 1/1982 |
| EP | 1053763 A2 | 11/2000 |

OTHER PUBLICATIONS

Sherwood, Gregory J., "Capacitor with Flexible Bus", U.S. Appl. No. 11/124,989, filed May 9, 2005, 30 Pages.

Sherwood, Gregory J., "Method and Apparatus for High Voltage Aluminum Capacitor Design", U.S. Appl. No. 11/182,707, filed Jul. 15, 2005, 239 Pages.

Sherwood, Gregory J., "Method and Apparatus for Providing Flexible Partially Etched Capacitor Electrode Interconnect", U.S. Appl. No. 60/588,905, filed Jul. 16, 2004, 241 Pages.

"International Search Report and Written Opinion for Application No. PCT/US2006/017819, dated Sep. 12, 2006", 11 Pages.

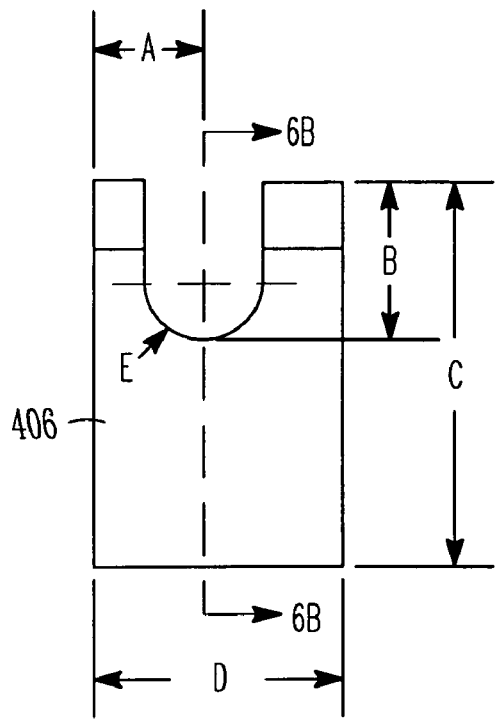 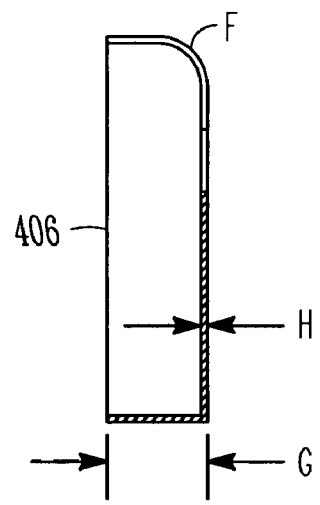
FIG. 6A  FIG. 6B
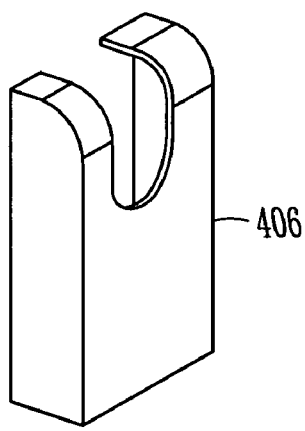
FIG. 6C

METHOD AND APPARATUS FOR INSULATIVE FILM FOR CAPACITOR COMPONENTS

CROSS REFERENCE TO RELATED APPLICATIONS

The present application is related to the following commonly assigned U.S. Patents which are incorporated by reference in their entirety: "High-Energy Capacitors for Implantable Defibrillators," U.S. Pat. Ser. No. 6,556,863, filed Oct. 2, 1998, issued Apr. 29, 2003; "Flat Capacitor for an Implantable Medical Device," U.S. Pat. Ser. No. 6,699,265, filed Nov. 3, 2000, issued Mar. 2, 2004. Additionally, the present application is related to the following Provisional U.S. patent application which is assigned to the same assignee and is incorporated by reference in its entirety: "Method and Apparatus for Single High Voltage Aluminum Capacitor Design," Ser. No. 60/588,905, filed on Jul. 16, 2004. Additionally, the present application is related to the following commonly assigned copending U.S. patent applications which are incorporated by reference in their entirety: "Capacitor Shell Including Two Mateable Cupped Components," Ser. No. 11/124,705.

TECHNICAL FIELD

This disclosure relates generally to capacitors, and more particularly, to a method and apparatus for insulative film for capacitor components.

BACKGROUND

There is an ever-increasing interest in making electronic devices physically smaller. Consequently, electrical components become more compact as technologies improve. However, advances in technology bring about additional problems. One problem involves constraining subcomponent layers in capacitors.

For example, capacitors with stacked layers require physical management in processing and in use so that the stack does not become misaligned. Layers are small, and vulnerable to bending or breaking. Improved methods of physical management should improve the stability of a selected arrangement of subcomponents in production and use, and should protect the components from damage. The systems used to constrain the multiple layers should be efficient, and readily adapted for manufacturing. Of further benefit would be a solution which could electrically isolate the stacked subcomponents from adjacent components or subcomponents.

Thus, there is a need in the art for a method and apparatus of constraining capacitor stack layers efficiently, so they are protected from damage and are electrically isolated from objects adjacent the capacitor stack.

SUMMARY

The above-mentioned problems and others not expressly discussed herein are addressed by the present subject matter and will be understood by reading and studying this specification.

One embodiment of the present subject matter includes an apparatus, comprising: a capacitor stack, including at least one substantially planar anode layer arranged in stacked alignment adjacent at least one substantially planar cathode layer, with at least one separator layer disposed therebetween; a conformed heat shrink film at least partially enveloping the capacitor stack in a bound state; a case with a first opening sized for receiving a capacitor stack, the case having at least one feedthrough opening; and a lid mateable to the first opening; wherein the capacitor stack is disposed in the case, the lid is sealably connected to the first opening, and electrolyte is disposed in the case.

Additionally, one embodiment of the present subject matter includes an apparatus, comprising: a capacitor stack, including at least one substantially planar anode layer arranged in stacked alignment adjacent at least one substantially planar cathode layer, with at least one separator layer disposed therebetween; thermally conformed heat shrink film means for enveloping the capacitor stack in a bound state; case for sealably housing the capacitor stack; and electrolyte disposed in the case.

One embodiment of the present subject matter includes a method, comprising: stacking into a capacitor stack at least one substantially planar anode layer onto at least one substantially planar cathode layer, with at least one separator layer disposed therebetween; aligning the at least one substantially planar anode layer to the at least one substantially planar cathode layer; at least partially enveloping the capacitor stack with at least one conformable heat shrink film; conforming the at least one conformable heat shrink film with a thermal process such that the capacitor stack is bound in stacked alignment; positioning the capacitor stack in a capacitor case having at least one feedthrough such that the capacitor stack is connected to the at least one feedthrough; disposing electrolyte in the capacitor case; and sealing the capacitor case.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIG. 6A is a front view of a connection member insulative sleeve, according to one embodiment of the present subject matter.

FIG. 6B is a front view of a connection member insulative sleeve, according to one embodiment of the present subject matter.

FIG. 6C is a front view of a connection member insulative sleeve, according to one embodiment of the present subject matter.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Figure 1:
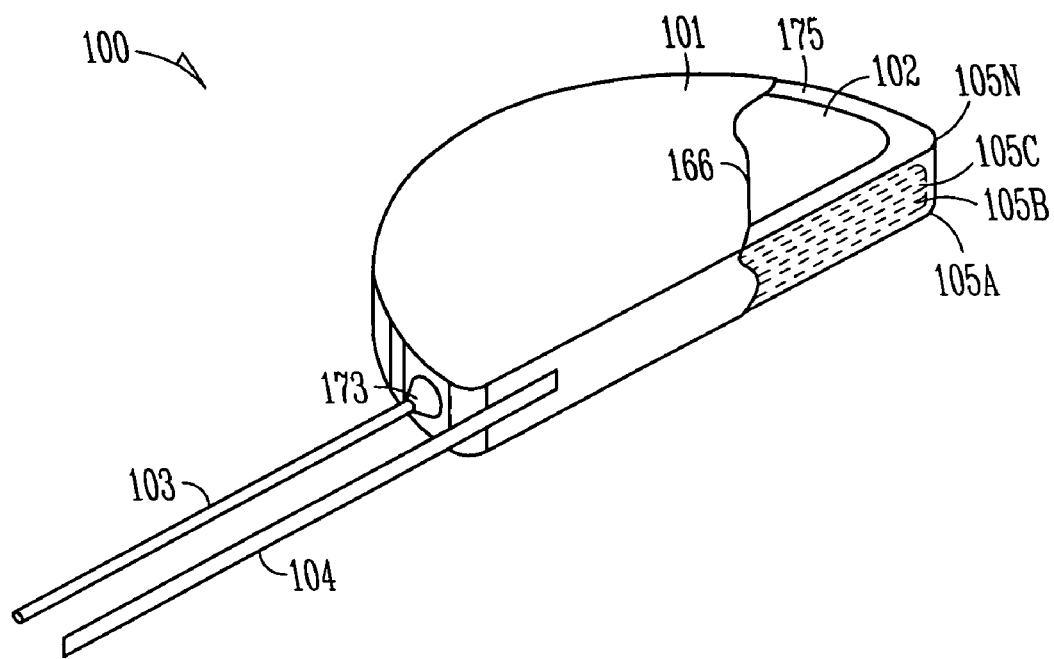
FIG. 1 is a perspective view of a capacitor, according to one embodiment of the present subject matter.

FIG. 1A shows a flat capacitor 100 constructed according to one embodiment of the present subject matter. Although capacitor 100 is D-shaped, in additional embodiments the capacitor is another desirable shape, including, but not limited to, rectangular, circular, oval or other symmetrical or asymmetrical shapes. Capacitor 100 includes a case 101 which contains a capacitor stack 102. In some embodiments, case 101 is manufactured from a conductive material, such as aluminum. In additional embodiments, the case 101 is manufactured using a nonconductive material, such as a ceramic or a plastic. The capacitor stack 102, in various embodiments, is constructed from planar anode, cathode, and separator subcomponents, as is discussed herein. In various embodiments, visible through break-line 166 is a perimeter film 175 binding the capacitor stack 102. Various conformed film embodiments are discussed in detail herein.

Capacitor 100 includes a first terminal 103 and a second terminal 104 for connecting capacitor stack 102 to an outside electrical component, such as heart monitor circuitry, including defibrillator, cardioverter, and pacemaker circuitry. In one embodiment, terminal 103 is a feedthrough terminal insulated from case 101, while terminal 104 is directly connected to case 101. Terminal 103 comprises an aperture in case 101, in various embodiments. Additionally, terminal 103 comprises a seal 173 in various embodiments. One embodiment of seal 173 includes epoxy. The capacitor incorporates additional connection structures and methods in additional embodiments. Connection structures and methods within the scope of the present subject matter are illustrated on pages 12-13, 59-60, 63-82 of related publication "Method and Apparatus for Single High Voltage Aluminum Capacitor Design," Ser. No. 60/588,905, filed on Jul. 16, 2004, incorporated herein in its entirety, but not by way of limitation.

Capacitor stack 102 includes a cathode, one or more separators, and an anode. In various embodiments, anodes are subdivided into multiple interconnected subcomponents, and cathodes are subdivided into multiple interconnected subcomponents. In some embodiments, these components are organized into capacitor elements 105a, 105b, 105c, ..., 105n, illustrated through break line 166. A capacitor element includes at least one anode layer subcomponent, and at least one cathode layer subcomponent. In various embodiments, multiple elements are interconnected. For example, in one embodiment a first element having a first anode layer is interconnected with a second element having a second anode layer, with the first anode layer and the second anode layer interconnected.

In various embodiments, stack 102 is formed in two steps, including a first step of stacking capacitor components into two or more elements 105a, 105b, 105c, ..., 105n, and a second step of stacking elements into a capacitor stack. Additional embodiments include forming a capacitor stack in a single step, or more steps. Related Provisional Patent Application "Method and Apparatus for Single High Voltage Aluminum Capacitor Design," Ser. No. 60/588,905, filed on Jul. 16, 2004 includes example methods and structure related to these configurations on pages 41-50, and is incorporated herein by reference, but not by way of limitation.

Each cathode subcomponent of capacitor stack 102, in various embodiments, is a metallic planar structure. Varying examples include a cathode layer connected to additional cathode layers using a variety of methods and structures, including welding. In some embodiments, the cathodes are coupled to case 101, and terminal 104 is attached to case 101, providing a connection between the cathode and outside circuitry. In some embodiments, the cathode is coupled to a feedthrough conductor extending through a feedthrough hole.

Capacitor stack 102 additionally includes one or more anode subcomponents, in various embodiments. Anodes can include aluminum, tantalum, hafnium, niobium, titanium, zirconium, and combinations of these metals, in various embodiments. In one embodiment, at least portions of a major surface of each anode subcomponent is roughened and/or etched to increase its effective surface area. This increases the capacitive effect of the anode on a volumetric basis, in some examples.

In various embodiments, each anode subcomponent is connected to other anode subcomponents of the capacitor, the connected anode subcomponents coupled to feedthrough assembly 103 for electrically connecting the anode to circuitry outside the case. In some embodiments, the anode is connected to the case and the cathode is coupled to a feedthrough assembly. In various embodiments, both the anode and the cathode are connected to components through one or more feedthroughs. Some of these electrode embodiments are not attached to the case.

In addition to cathodes and anodes, various embodiments include one or more separators positioned, in part, to insulate capacitor stack components. One or more separators are used to insulate each anode from each cathode, for example. In various embodiments, the separator includes one or more sheets of kraft paper impregnated with an electrolyte. Varying forms of electrolyte includes a fluidic compound adapted for use in a capacitor. Examples with electrolyte include any electrolyte for an electrolytic capacitor, such as an ethyleneglycol base combined with polyphosphates, ammonium pentaborate, and/or an adipic acid solute.

Anodes, cathodes, separators, and additional components within the art are disclosed in commonly assigned related Provisional U.S. Patent Application: "Method and Apparatus for Single High Voltage Aluminum Capacitor Design," Ser. No. 60/588,905, which was filed Jul. 16, 2004 and which is incorporated by reference herein, not by way of limitation, at pages 29-34. These embodiments comprise a capacitor stack adapted to deliver between 7.0 Joules/cubic centimeter and 8.5 Joules/cubic centimeter, in various embodiments. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the capacitor stack is disposed in a case, and linked with other components, a state which affects some of these values. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules. In various embodiments, these ranges are available at a voltage of between about 410 volts to about 610 volts.

Figure 2:
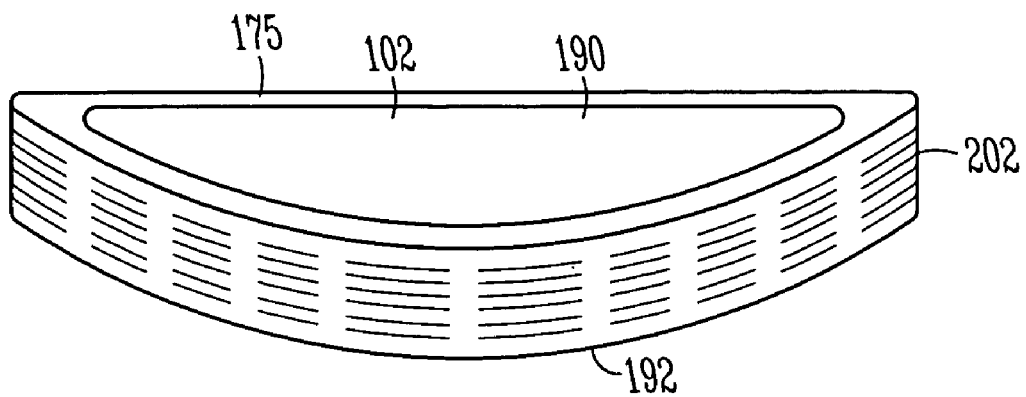
FIG. 2 is a perspective view of a capacitor stack, according to one embodiment of the present subject matter.

FIG. 2 is a perspective view of a capacitor stack, according to one embodiment of the present subject matter. The figure illustrates a perimeter film 175 embodiment of a conformed film. Capacitor stack 102 is comprised of a series of layers, pictured in hidden lines, in various embodiments. In various embodiments, the perimeter film 175 is used where the capacitor stack 102 exterior comprises an edge surface 202 extending between a top layer 190 and a bottom layer 192, with the top layer and the bottom layer in substantially parallel alignment. The perimeter film 175 envelopes the edge surface 202, in various embodiments.

Conformable films, including the perimeter film 175, in various embodiments, are of a heat shrink film variety. Additional embodiments include a thermoformed variety. Thermoformed embodiments use various materials, including polyvinyl chlorides (PVC), polyolefins, polysulfones, polyethersulfones, polyesters, polyetherimides, TEFLON and material using TEFLON, including PFAs, and PTFAs, polytetrafluoroethylenes (PTFE), polyimides, and polyethylene terephthalate glycols (PETG). TEFLON is a registered trademark of the E.I. DuPont de Nemours and Company Corporation, 101 West 10$^{th}$ St., Wilmington, Del. 19898. Various embodiments include parts formed at temperatures ranging from about 150 degrees centigrade to about 250 degrees centigrade. Time durations for forming thermoformed parts are variable depending on the shape of the part and the material requirements.

In heat shrink film embodiments, the final conformed heat shrink film starts out as a ring shaped or tube shaped film. Some embodiments have a seam extending parallel along the axial length of the tube. Additional embodiments are seamless. Seamless varieties offer various advantages over seam embodiments, but are not widely available. Heat shrink film 175, in various embodiments, is conformed to a capacitor stack 102. This involves fitting the heat shrink film 175 to the capacitor stack 102, and then shrinking the heat shrink film 175 to the capacitor stack 102, in various embodiments. In some embodiments, the tube walls substantially abut the edge 202 of the capacitor stack 102. The film is conformed to the capacitor stack such that the capacitor stack is bound, in various embodiments. Various heat shrink films fall within the scope of the present subject matter. One heat shrink film comprises polyethylene terephthalate (PET). Various additional polymers include polyolefins, polyimides, MYLAR, PTFE, PVC, fluorinated ethylene propylene (FEP), perfluoroalkoxy (PFA), ethylene tetrafluoroethylene copolymer (ETFE), PETG, or combinations of these polymers. MYLAR is a registered trademark of the E.I. DuPont de Nemours and Company Corporation, 101 West 10$^{th}$ St., Wilmington, Del. 19898.

In various examples, heat shrink film is colorless. Some colorless embodiments are substantially transparent. Substantially transparent heat shrink films are difficult to manage in processing and use, because they are hard to see. In some of these embodiments, a tint or coloring is added to the heat shrink film. A tint or coloring for a heat shrink film allows a user to see the film during handling and in use.

Conforming the film includes "heat shrinking", in various embodiments. Various examples of this process involve heating the plastic, once installed to a capacitor stack, with a heat source. Various embodiments use convection heat sources, but additional sources utilize heat radiation or combinations of heat radiation and convection. Various methods of heat shrinking are within the scope of the present subject matter. Some heat the heat shrink film with a heat source at a temperature ranging from about 150 degrees Centigrade to about 250 degrees Centigrade. The duration of heating ranges from about 10 seconds to about 10 minutes. In some embodiments, a cooling period of approximately 5 minutes is used to allow the material to stabilize before subjecting the capacitor stack 102 to downstream processing steps.

Heat shrink films having various properties are within the scope of the present subject matter. Some heat shrink configurations are adapted to shrink at a first rate in a first direction, and to shrink at second rate in a second direction. In various embodiments, the material shrinks at a universal, consistent rate. In one embodiment, the material shrinks at or less than approximately a 3.7:1 ratio. In some embodiments, the material shrinks in a first direction from about 0 to about 3:1 in a direction parallel the first major surface. In some of these embodiments, the material shrinks approximately 0 in a second direction, orthogonal to the first direction. In some of these embodiments, if the second direction were greater than approximately zero, the perimeter would not envelope the edge surface 202.

Heat shrink tubes or films of varying thicknesses are within the scope of the present subject matter. For example, tubes with a tube wall thickness of from about 0.0005 inches to about 0.002 inches are within the scope of the present subject matter. Tubes are fitted to capacitor stacks in varying ratios of capacitor stack perimeter to tube circumference. Examples of tubes fitted to capacitor stacks include to ratios of tube circumference to perimeter length of from about 0.95:1 to about 1.1:1. A parts combination with a 0.95:1 unshrunk tube volume to capacitor stack volume ratio requires some stretching of the heat shrink film before fitting it to the capacitor stack.

Additionally, various embodiments of the present subject matter include thermoformed conformed films. Thermoforming results in parts which are preformed before installation to other components. The preformed materials are thermoformed plastics, in various embodiments. Thermoformed embodiments use various materials, including polyvinyl chlorides (PVC), polyolefins, polysulfones, polyethersulfones, polyesters, polyetherimides, TEFLON and material using TEFLON, including PFAs, and PTFAs, polytetrafluoroethylenes (PTFE), polyimides, and terephthalate glycols (PETG). TEFLON is a registered trademark of the E.I. DuPont de Nemours and Company Corporation, 101 West 10$^{th}$ St., Wilmington, Del. 19898. Various embodiments include parts formed at temperatures ranging from about 150 degrees centigrade to about 250 degrees centigrade. Time durations for forming thermoformed parts are variable depending on the shape of the part and the material requirements. Various embodiments are electrically insulative. For example, in some embodiments, one or more conformed films are disposed between a capacitor stack and a conductive case, electrically insulating the capacitor stack from the conductive case.

Figure 3A:
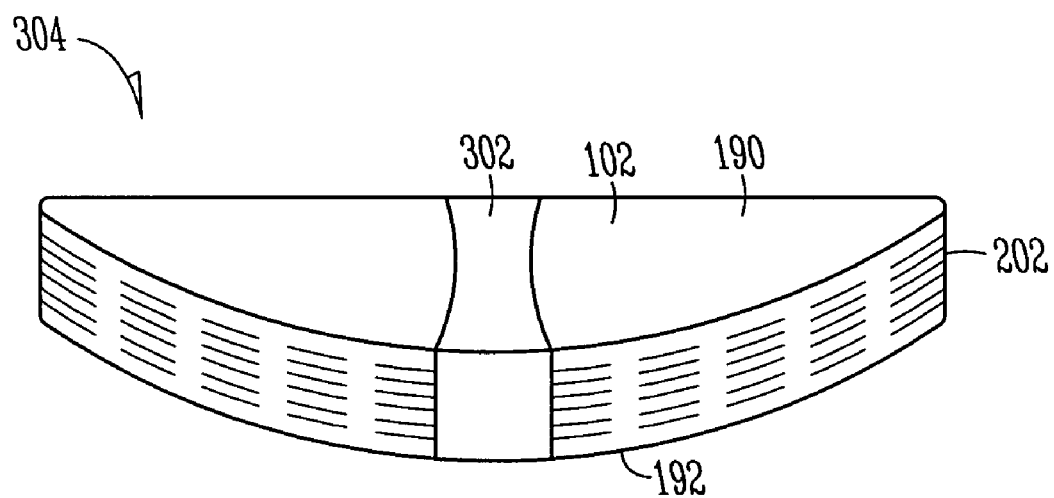
FIG. 3A is a perspective view of a capacitor stack and associated components, according to one embodiment of the present subject matter.

FIG. 3A is a perspective view of a capacitor stack, according to one embodiment of the present subject matter. Various embodiments include a band film 302 conformable film binding capacitor stack 102. In various embodiments, the band film 302 is a heat shrink film. In various embodiments, the conformed band film 302 is banded around the capacitor stack 102, with the band film 302 crossing a top layer 190 and a bottom layer 192, and portions of the edge surface extending between the top layer 190 and the bottom layer 192. Band film 302, in some embodiments, is tube shaped, and extends around the center of a flat capacitor stack orthogonal to the perimeter edge 202 of the flat capacitor stack. In various embodiments, the band film 302 is fitted 304 over the top of a capacitor stack 102 in an unconformed state, and is then conformed to the stack 102.

The illustrated band film 302 has curvilinear aspects. In various embodiments, the film in an unconformed state does not present these aspects. The curvilinear aspects, in various embodiments, are a product of non-linear contraction rates of some heat shrink films. Various embodiments of the present subject matter are specially designed to compensate for these non-linear contraction rates. For example, in some embodiments, a band film which has yet to be conformed to a capacitor stack has a circumference ranging from about 95% of the size of the material to be enveloped to about 110% of the size of the material. In various embodiments, the width of the band film is from 0.25 inches to about 1.25 inches. The width is selected to ensure that a conformed band film 302 is robust in capacitor stack processing and use.

In various embodiments, the band film is combined with other conformed films. For example, in some embodiments, a perimeter heat shrink film is combined with a band heat shrink film. Other configurations are possible as well. In some of these embodiments, all of the band films are shrunk at once using a heat shrink process. In additional embodiment, the films are conformed sequentially, using sequential heat shrink processes. These exact recitations are not intended to be limiting, and combinations of concurrent and sequential operations are possible without departing from the scope of the present subject matter.

Figure 3B:
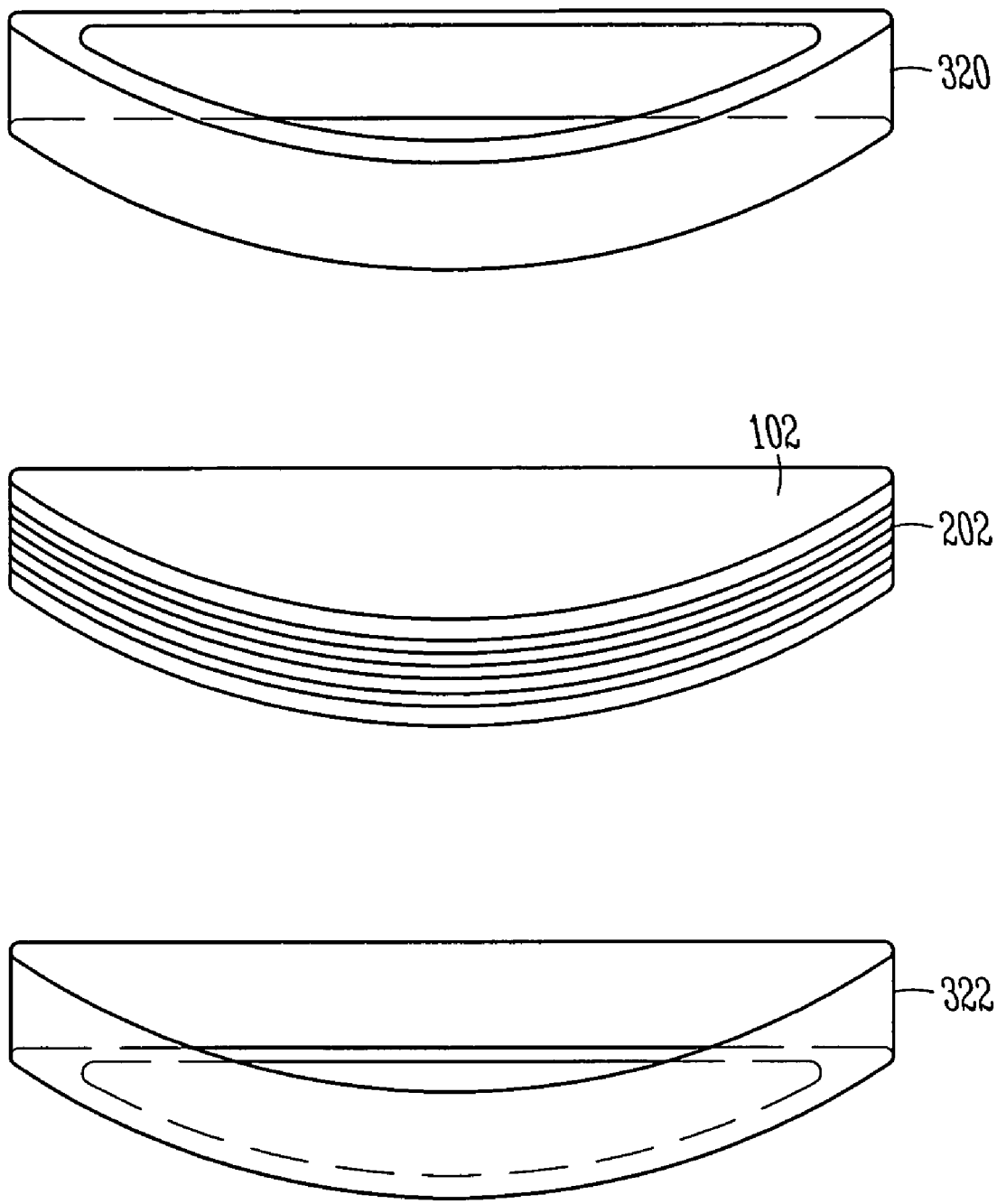
FIG. 3B is an exploded, perspective view of a capacitor stack and associated components, according to one embodiment of the present subject matter.

FIG. 3B is an exploded, perspective view of a capacitor stack and associated components, according to one embodiment of the present subject matter. In various embodiments, a band film is disposed around a capacitor stack which is partially encapsulated by one or more preformed shells. Other embodiments combine a band film with a perimeter film which is conformed to the edge 202 of capacitor stack 102. In one embodiment, the preformed shells include a top portion 320 and a bottom portion 322. The illustrated preformed shells are of a heat shrink variety, but the present subject matter is not so limited. For example, thermoformed shells may be used. Some embodiments of preformed shells include conformed heat shrink films which are first shrunk to a mandrel, and then which are removed from the mandrel and applied to a capacitor stack.

Figure 3C:
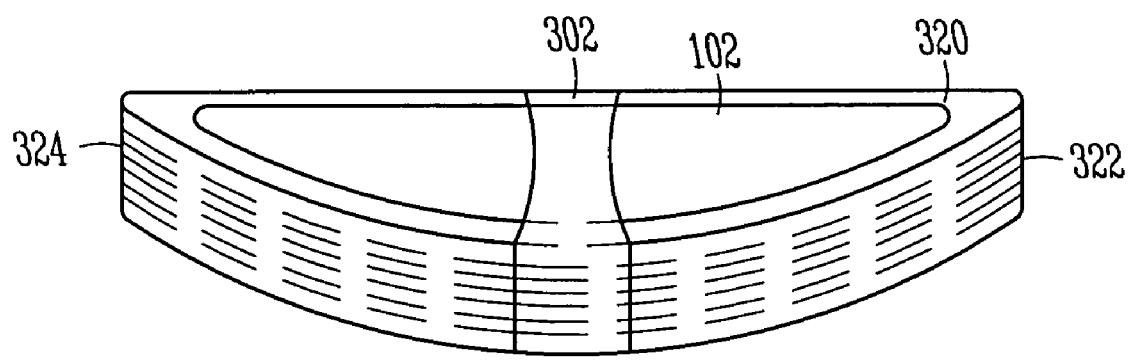
FIG. 3C is a perspective view of a capacitor stack and associated components, according to one embodiment of the present subject matter.

FIG. 3C is a perspective view of a capacitor stack, according to one embodiment of the present subject matter. The preformed shells may touch in a use position, or they may not. In one embodiment, the preformed films intersect in a use position with a lap joint 324. But other configurations, such as a butt joint, are also possible.

Arranging perimeter film with a band film 302 as such has various benefits. One benefit is improved dimensional stability of a capacitor stack. A perimeter film does not bind the capacitor stack using the same forces as does a band film 302. For example, in one embodiment, the thermoformed parts keep the layers in stacked alignment, while the band film 302 stabilizes the alignment. Additionally, small details are covered more extensively in some embodiments using formed thermoformed parts with small, articulate features impossible to envelope with a single heat shrink film.

Figure 4A:
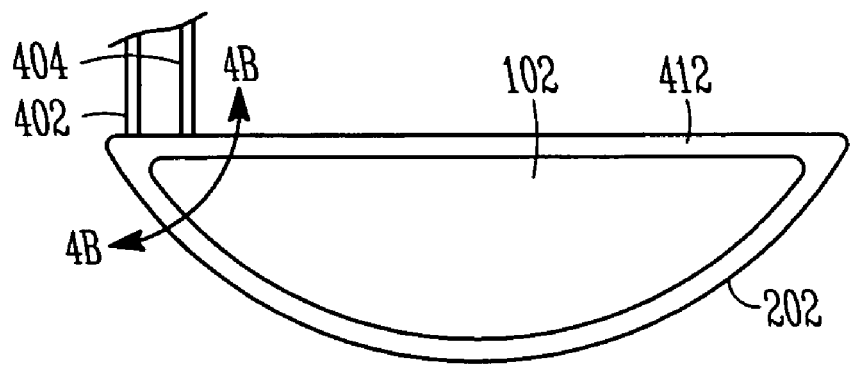
FIG. 4A is a top view of a capacitor stack and associated components, according to one embodiment of the present subject matter.

FIG. 4A is a top view of a capacitor stack, according to one embodiment of the present subject matter. The illustration is a diagram illustrating one configuration, and is intended to demonstrate the location of various components. Visible in the diagram is a capacitor stack 102, a perimeter film 412, a first terminal 402, and a second terminal 404. In various capacitor embodiments, the perimeter film encircles the capacitor, disposed along the edge 202 of the capacitor.

Figure 4B:
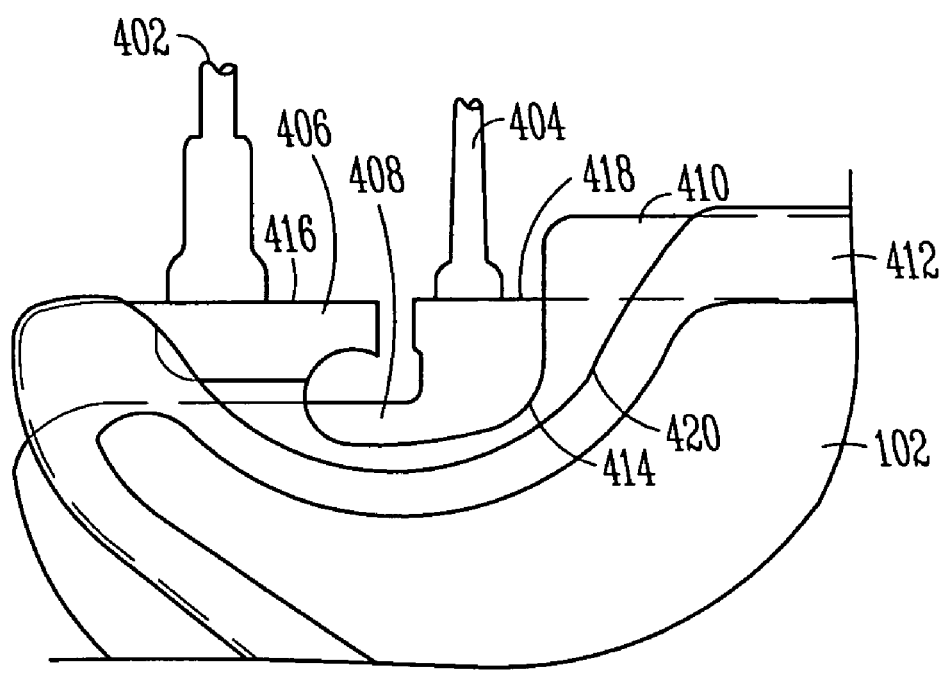
FIG. 4B is a sectional top view of a capacitor stack taken at line "4B" of FIG. 4A, according to one embodiment of the present subject matter.

FIG. 4B is a sectional top view of a capacitor stack according to one embodiment of the present subject matter, with the sectional taken at line "4B" of FIG. 4A. This illustration includes more detail than does FIG. 4A. This section view includes details related to connection members, two types of insulators, terminals, and how they are arranged with respect to one anther. The capacitor stack includes anode 410 and cathodes 408. These subcomponents are arranged in a stack. The subcomponents differ slightly in their shape so that anode connection members can extend away from the capacitor stack in one position, and cathode connection members extend away from the capacitor stack in another position. For example, the anodes define a cut-out 414. Visible through the cut-out, in various embodiments, are one or more cathodes 408.

In various embodiments, the capacitor electrodes are shaped and stacked in an arrangement such that they define a connection surface. For example, the one or more anodes 410 define an anode connection surface 416. The one or more cathodes 408 define a cathode connection surface 418. These surfaces may be planar or have a nonplanar contour. Methods and structure form connection surfaces are outlined at pages 12-17, 23-29, 65-79, and 97-100 of related Provisional U.S. Patent Application which is commonly assigned and is incorporated herein by reference not by way of limitation:

"Method and Apparatus for Single High Voltage Aluminum Capacitor Design," Ser. No. 60/588,905, filed on Jul. 16, 2004.

Various capacitor embodiments include a perimeter film 412. The perimeter film 412, in various embodiments, includes an opening 420. An opening can be formed a number of ways. A perimeter film 412 can have material excised from it to form an opening, in various embodiments. Additionally, in various embodiments, it can be pierced. In additional embodiment, the tubing in an unconformed state may be slit, with the slit expanding into an aperture as the tubing conforms to the capacitor stack. The opening 420, in various embodiments, is sized for allowing access to an anode connection surface 416 and a cathode connection surface 418. In various embodiment, opening 420 is adapted for the passage of a terminal connected to the capacitor stack.

Figure 5A:
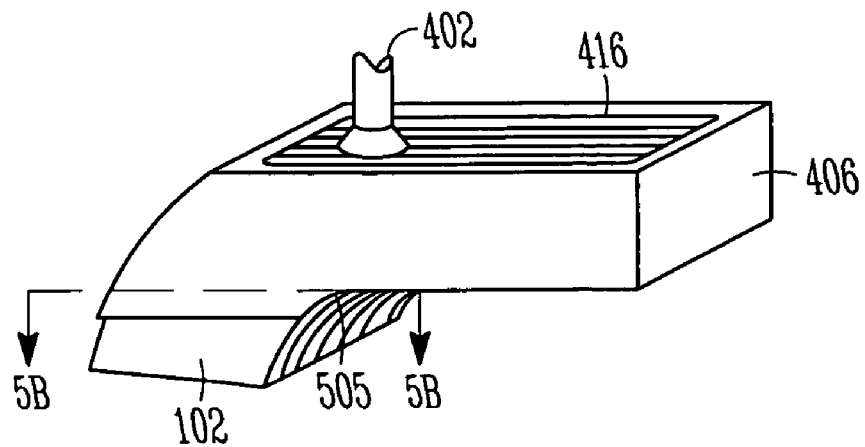
FIG. 5A is a perspective view of a portion of a capacitor stack including connection members, according to one embodiment of the present subject matter.

In various embodiments, the capacitor includes a connection member insulative sleeve 406. The connection member insulative sleeve can be of a heat shrink variety, or can be thermoformed. The connection member insulative sleeve 406 can be preformed, or it can be conformed after being installed to the connection members. One embodiment of a connection member insulative sleeve formed by fitting a preformed insulative piece to the anode connection members is disclosed in FIG. 5A. FIG. 5A is a perspective view of a portion of a capacitor stack 102 including anode connection members defining an anode connection surface 416, according to one embodiment of the present subject matter. The illustration additionally shows a terminal 402 connected to the anode connection surface 416. The preformed connection member insulative sleeve extends to recessed areas such as area 505. The shape and configuration of the connection member insulative sleeve is selected, in various embodiments, to prevent breakdown from occurring.

Figure 5B:
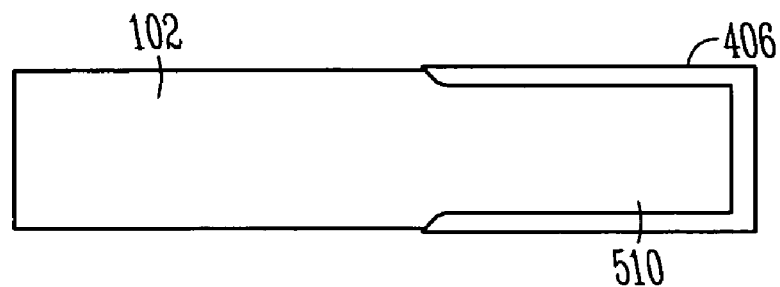
FIG. 5B is a bottom view of a portion of a capacitor stack including connection members, according to one embodiment of the present subject matter.

FIG. 5B is a bottom view of a portion of a capacitor stack 102, including connection members, according to one embodiment of the present subject matter. In one embodiment, a preformed insulative component 406 defines an opening 510. An opening, in various embodiments, can ease assembly of the preformed part to the capacitor.

FIG. 6A is a front view of a connection member insulative sleeve 406, according to one embodiment of the present subject matter. FIG. 6B is a side view of a connection member insulative sleeve 406 taken at the line "6B" in FIG. 6A, according to one embodiment of the present subject matter. For reference, the illustration includes various dimensions. For example, in one embodiment, dimension A is approximately 0.068 inches. Dimension B is approximately 0.097 inches, in various embodiments. In additional embodiments, dimension C is approximately 0.239 inches. Dimension D is approximately 0.152 inches, in various embodiments. Radius dimension E is approximately 0.037 inches, in various embodiments. FIG. 6C is a front view of a connection member insulative sleeve 406, according to one embodiment of the present subject matter. For reference, the illustration includes various dimensions. For example, in one embodiment, radius dimension F is approximately 0.035 inches. Dimension G is approximately 0.060 inches, in various embodiments. In additional embodiments, dimension H is approximately 0.003 inches to 0.007 inches.

Figure 7A:
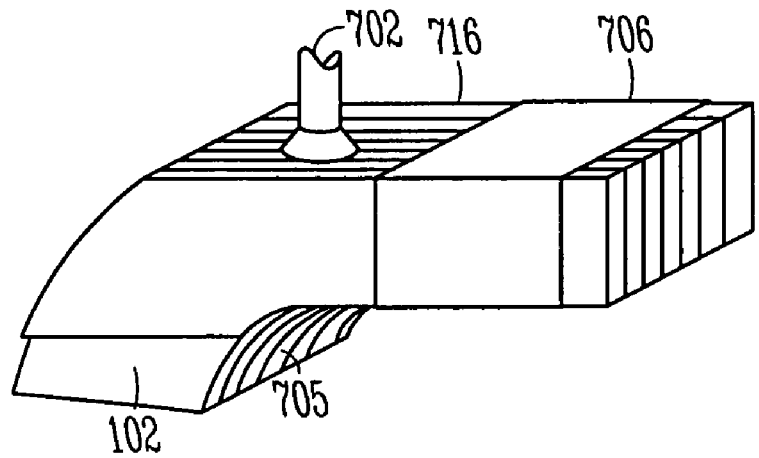
FIG. 7A is a perspective view of a portion of a capacitor stack including connection members, according to one embodiment of the present subject matter.

FIG. 7A is a perspective view of a portion of a capacitor stack including connection members, according to one embodiment of the present subject matter. In various embodiments, the capacitor stack 102 includes a connection member insulative sleeve 706. In various embodiments, the connection member insulative sleeve 706 is a heat shrink film. The connection member insulative sleeve 706 is conformed after being installed to the connection members, in various embodiments. The illustration additionally shows a terminal 702 connected to the connection surface 716. The connection member insulative sleeve 706 extends to recessed areas such as area 705. The shape and configuration of the connection member insulative sleeve is selected, in various embodiments, to prevent breakdown from occurring.

Figure 7B:
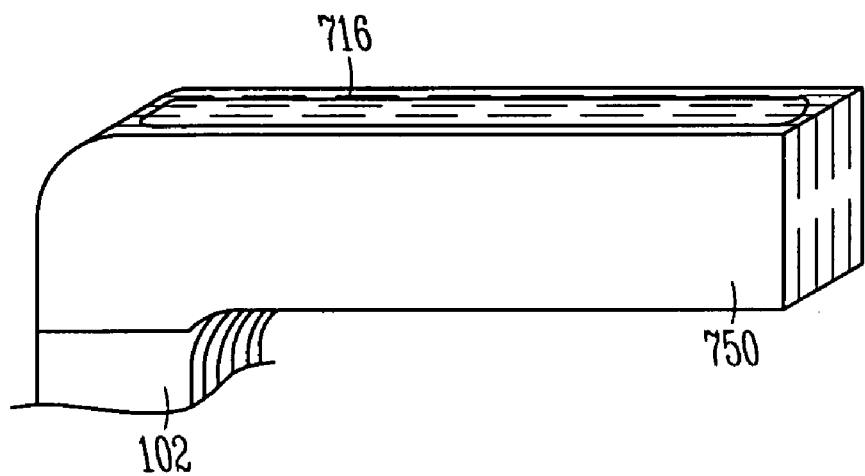
FIG. 7B is a perspective view of a portion of a capacitor stack including connection members, according to one embodiment of the present subject matter.

FIG. 7B is a perspective view of a portion of a capacitor stack including connection members, according to one embodiment of the present subject matter. In various embodiments, the capacitor stack 102 includes a connection member conformed heat shrink film 750. The illustration additionally shows a connection surface 716.

Figure 8A:
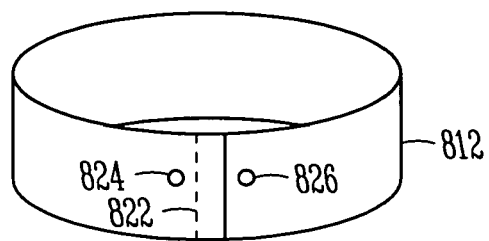
FIG. 8A is a perspective view of a heat shrink film, according to one embodiment of the present subject matter.

FIG. 8A is a perspective view of a heat shrink film, according to one embodiment of the present subject matter. In various embodiments, heat shrink film 812 is adapted for use as a perimeter film. The embodiment illustrated has yet to be shrunk. In various embodiments, the heat shrink film is formed from a sheet of heat shrink material, which is joined to itself at a seam 822. Other embodiments, however, are within the scope of the present subject matter, such as embodiments which cut from a seamless tube of heat shrink material a heat shrink film for use as a perimeter film. In seam embodiments, the seam can be created in a number of ways, including using thermal deformation or a solvent to join the material.

In various embodiments openings 824, 826 are provided for feedthroughs to a capacitor which is enveloped by the heat shrink film 812. In various embodiments, the openings are created when material is excised from the heat shrink film 812 prior to conforming the heat shrink film to a capacitor stack. In additional embodiments, the openings are formed by piercing the heat shrink film 812. A typical piercing does not remove material, but displaces it. In various embodiments having piercings, when the heat shrink film is conformed to a capacitor stack, the piercings grow into larger openings sized for passage of a feedthrough.

Figure 8B:
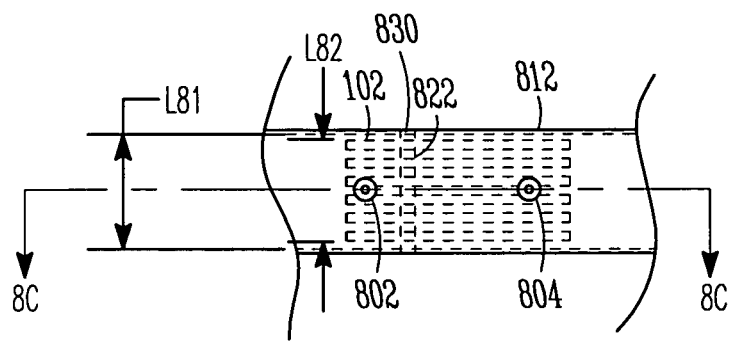
FIG. 8B is a partial front view of a capacitor stack enveloped by a heat shrink film, according to one embodiment of the present subject matter.

FIG. 8B is a partial front view of a capacitor stack enveloped by a heat shrink film, according to one embodiment of the present subject matter. FIG. 8B is an alternate view of FIG. 8A. Heat shrink film 812 is visible. Also visible is capacitor stack 102, which in various embodiments includes a plurality of layers not illustrated. Additionally visible are feedthroughs 802, 804, which are adapted for passage through a case for the capacitor stack 102. Seam 822 is shown.

In the present embodiment, the seam 822 displaces material toward the capacitor stack, instead of away form the capacitor stack. This is design feature is illustrated by lap joint 830. Configuring the lap joint as such creates a uniform exterior of a heat shrink film 812 in use. A uniform exterior, in various embodiments, is space efficient. One way to enable a uniform exterior, and an inward oriented lap joint 830, is to provide a plurality of connections members which are aligned and pressed together have a thickness L82 which is smaller than the thickness L81 of the capacitor stack 102. This reduced thickness provides a volume into which the seam 822 can be disposed. In various embodiments, this configuration compensates for the heat shrink film having double thickness in areas near the seam 822.

Figure 8C:
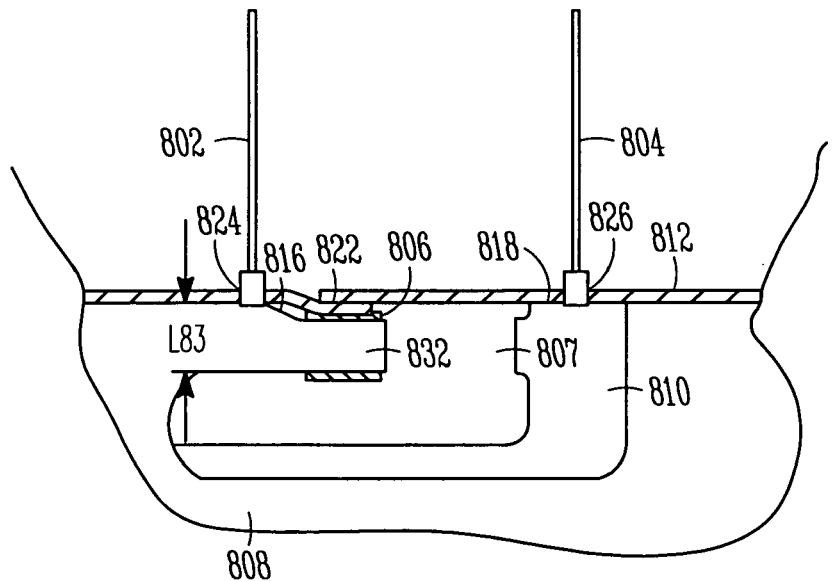
FIG. 8C is a cross section, taken at line "8C" of FIG. 8B, of a capacitor stack enveloped by a heat shrink film, according to one embodiment of the present subject matter.

FIG. 8C is a cross section, taken at line "8C" of FIG. 8B, of a capacitor stack enveloped by a heat shrink film, according to one embodiment of the present subject matter. The embodiment in this view of FIG. 8B shows the configuration of an anode 808 and a cathode 810. The anode and the cathode are in a stack having additional electrodes, with the stack extending into the page.

The embodiment in this view shows an inward displacement of seam 822. The illustration shows seam 822 and its location proximal connection members 832. The illustrated connection members 832 have a varying width L83, but embodiments with a constant width are within the scope of the present subject matter. The illustration demonstrates how feedthroughs 802, 804, are respectively connected through openings in the heat shrink film 824, 826, which are respectively aligned with connection surfaces 816, 818.

The embodiment illustrated additional demonstrates insulative sleeve 806. In various embodiments, the insulative sleeve 806 is a heat shrink tube conformed to connection members 832, but other embodiments are within the present subject matter. For example, preformed thermoformed pieces fit to connection members 832 are additionally within the scope of the present subject matter. The insulative sleeve 806 is provided, in various embodiments, to fortify electrical insulation provided by air gaps between the anode 808 and the cathode 810.

In additional embodiments, the seam 822 may be positioned in the gap 807, which provides a relief which is adapted to receive the seam in a manner which allows the seam to project inward, toward the capacitor stack. Various embodiments also provide a channel to receive the seam 822. A channel may be excised from the capacitor stack. In one embodiment, a seam shaped channel is laser cut from the capacitor stack.

Figure 9:
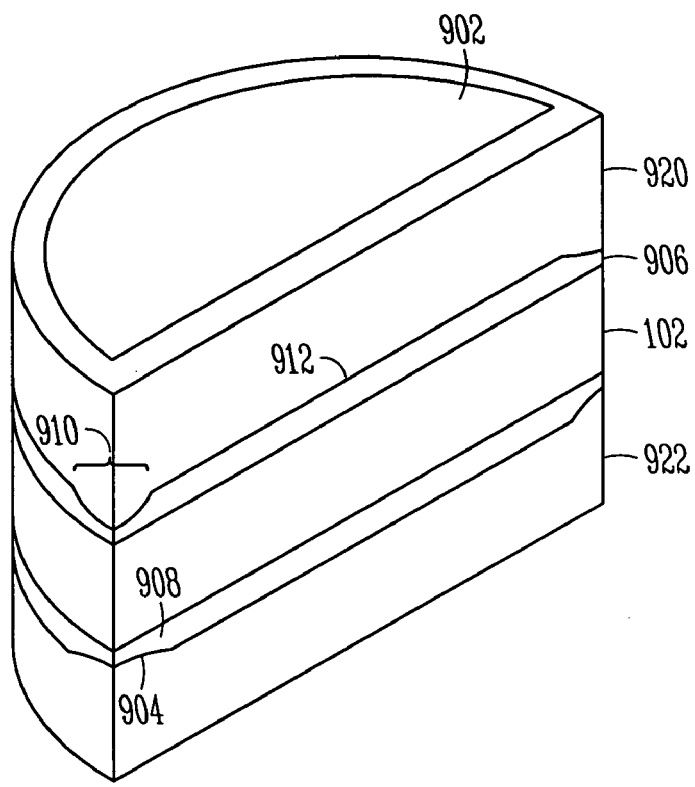
FIG. 9 is a perspective view of a preforming system, according to one embodiment of the present subject matter.

FIG. 9 is a perspective view of a preforming system, according to one embodiment of the present subject matter. A preforming system, in various embodiments, is fitted with one or more heat shrink films which are conformed with a heat shrinking process, and then removed for application to a capacitor stack 102, in various embodiments. The apparatus includes an inside top weight 902, a top preformed part 920, a first cut-line 906, and a capacitor stack 102, according to various embodiments. Additional embodiments include a bottom cut line 904, a bottom weight 908, and a bottom preformed part 922.

Cut lines 904, 906, in various embodiments, are useful for creating features such as corner extension shaped by corner extension cut line 910. A corner extension is useful in a variety of applications. For example, in some embodiments, the contraction of the preformed parts 920, 922 is not linear. Through use of a corner extension, a final shape can be achieved despite nonlinear contraction. In one example, the portions of the top preformed part 920 comprising the corner extension 910 become continuously linear with other portions of the top preformed part 920, such as edge 912.

In various embodiments, the upper weight 902 and the lower weight 908 are useful in manufacturing. Because a capacitor stack 102, in various embodiments, is not bound during aspects of manufacturing, capacitors stack 102 subcomponents, such as anode layers, cathode layers, and separator layers, are free to move with respect to each other. A weight such as upper weight 902 can hold these components in place during manufacturing operations such as batch operations. Although the illustration includes an upper weight 902 and a lower weight 908, embodiments using solely an upper weight are within the scope of the present subject matter.

Figure 10:
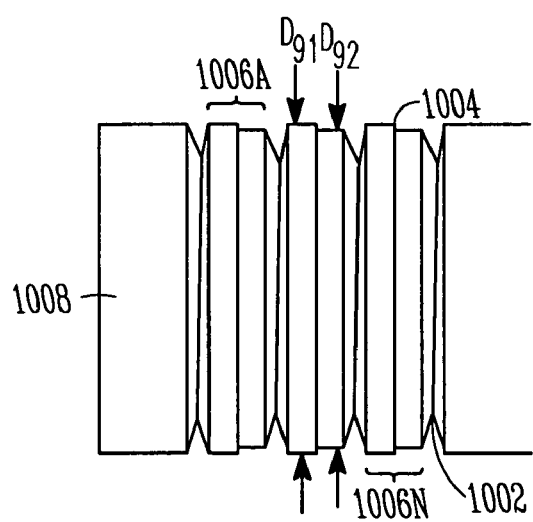
FIG. 10 is a perspective view of a preforming apparatus, according to one embodiment of the present subject matter.

FIG. 10 is a front view of a preforming mandrel, according to one embodiment of the present subject matter. In varying embodiments, the mandrel 1008 includes one forming pattern 1006A, or multiple forming patterns 1006A, . . . , 1006N. Within a forming pattern are shapes to which a conformable film can be contoured. For example, in one embodiment, a sheet or tube of heat shrinkable material is wrapped around a mandrel 1008. The material is heat shrink conformed to the mandrel 1008, in some embodiments. In some of these embodiments, the material is cut into portions. Cuts occur along a cut line 1002, in some examples. In various embodiments, cut line 1002 is adapted to guide a blade, and includes indentations adapted as such.

In various embodiments, a preforming mandrel includes a first diameter D91 and a second diameter D92. The first diameter D91 and the second diameter D92 can be of a matching profile in some embodiments, while other embodiments include varying diameters. In varying diameter embodiments, it is possible to create a first preformed shape and a second preformed shape which are mateable and intersect along a lap joint. Transitions between a first diameter D91 and a second diameter D92 can include a step 1004, but other gradient shapes are within the scope of the present subject matter, such as curves. Overall, by including a die with multiple preforming patterns, it is possible to make a large number of preformed parts efficiently. For example, a single conformable film tube can be mated to die 1008, and then conformed to the die. Additionally, the conformed film can be cut away from the die 1008 and into components used for binding a capacitor stack.

Figure 11:
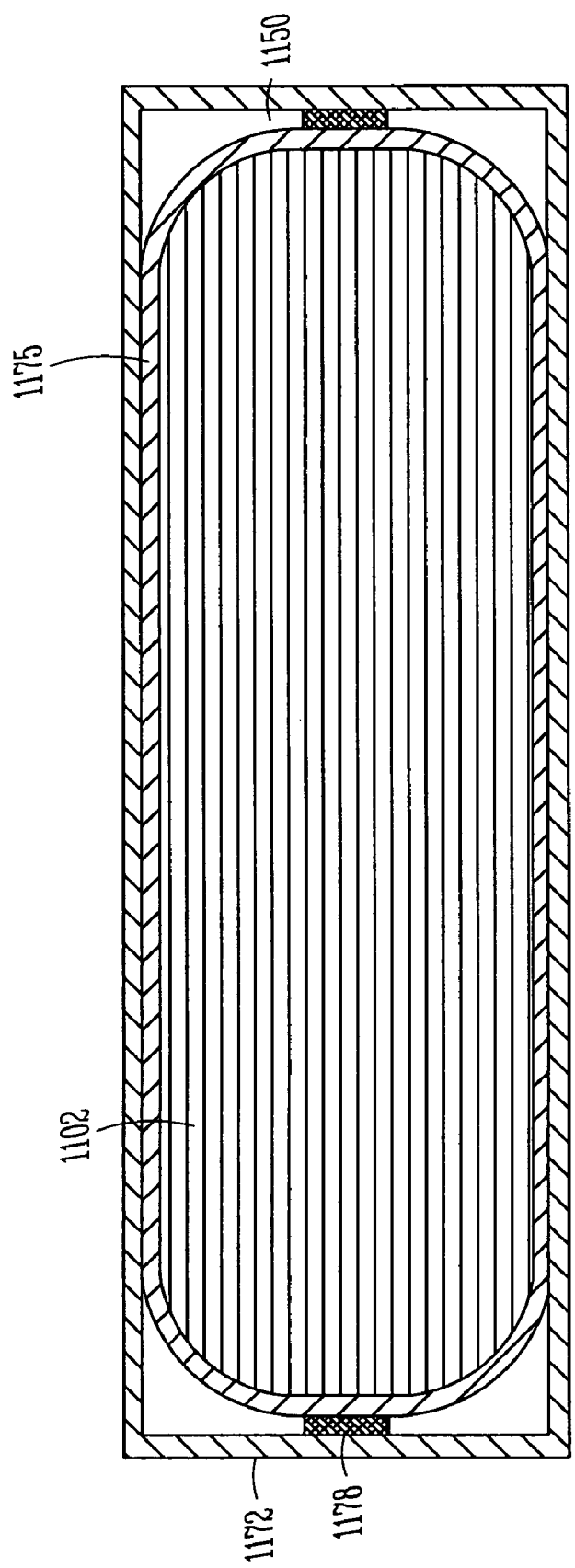
FIG. 11 is a cross section of a capacitor, according to one embodiment of the present subject matter.

FIG. 11 is a cross section of a capacitor, according to one embodiment of the present subject matter. Various embodiments include a capacitor stack 1102 disposed in a case 1172. Although these capacitor components comprise a rectangular shaped cross section, other embodiments are within the scope of the present subject matter, including those with an ovoid cross section, or those with a cross section shaped otherwise. It is important to note that the present subject matter is not limited to symmetrical embodiments: asymmetrical embodiments are also within the scope of the present subject matter, and can be used to better match some device space requirements.

Various embodiments include a backing plate 1178. A backing plate 1178, in various embodiments, is used as a structural element of the capacitor. For example, if a backing plate 1178 is attached to a first piece of a two-piece shell, it can be used in the alignment of the second piece. Additionally, backing plate 1178 is useful in joining processes for capacitor components, in various embodiments. For example, a backing plate 1178 can help reduce harmful effects of laser welding. Lasers used to join case portions, in various embodiments, can refract, and damage other capacitor components. A backing plate 1178 can reduce instances of refraction, reducing incidents of damage occurring during laser welding. Although backing plate 1178 is shown as a ring with a rectangular cross section disposed outside a conformed film 1175, the subject matter is not so limited. Additionally, while space 1150 is present in the illustrated embodiment, it does not exist in other configurations. Combinations of capacitor stacks and shells are shaped, in various embodiments, to eliminate space 1150.

Other embodiments incorporating welding are possible as well. Some embodiments position a backing ring 1178 around a capacitor stack 1102, and then conform a conformed film 1175 to the capacitor stack and ring. The conformed film, in various embodiments, is a heat shrink film. Various embodiments also include films produced using thermoforming.

Figure 12:
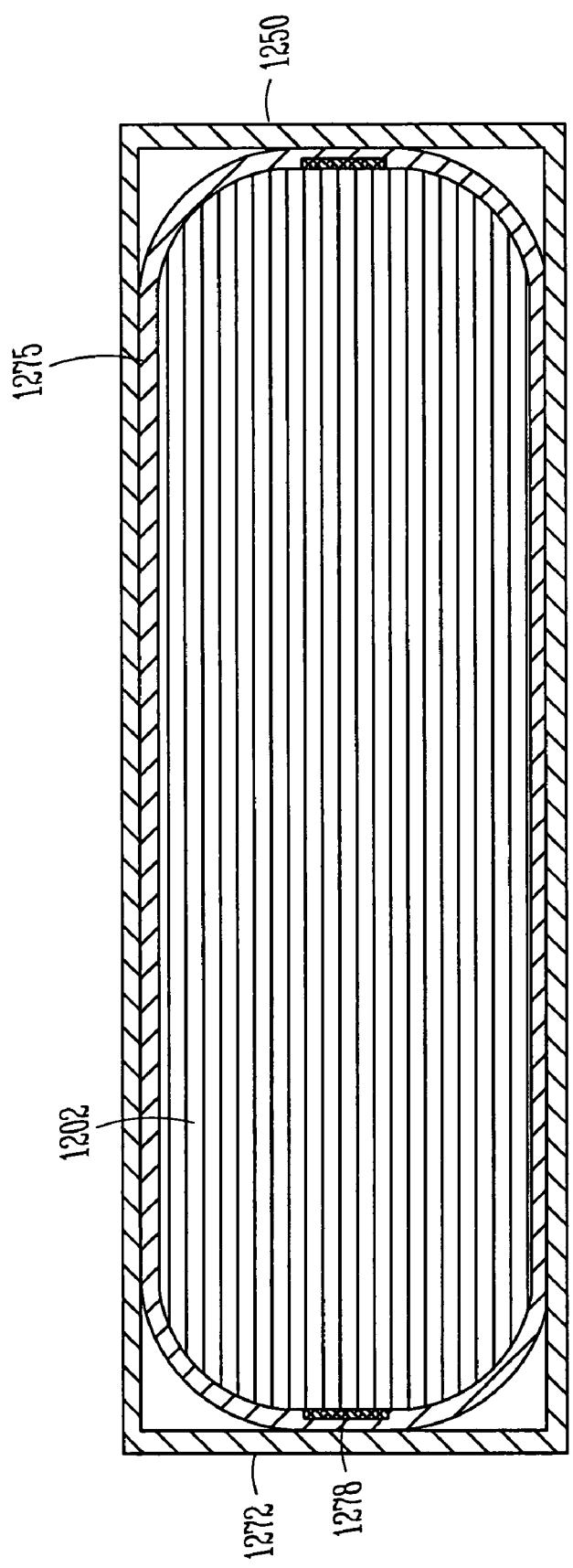
FIG. 12 is a cross section of a capacitor, according to one embodiment of the present subject matter.

FIG. 12 is a cross section of a capacitor, according to one embodiment of the present subject matter. Various embodiments include a capacitor stack 1202 disposed in a case 1272. Although the cross section shows components which are shaped rectangularly, other shapes are within the scope of the present subject matter. The backing ring 1278 is positioned within a conformed film 1275 in this embodiment. Space 1250 results from packaging inefficiencies, but this space does not exist in some embodiments with improved packaging efficiency.

In addition to embodiments where a backing ring is outside or inside a conformable film with respect to a capacitor stack covered by the film, various embodiments do not use a backing ring.

Figure 13:
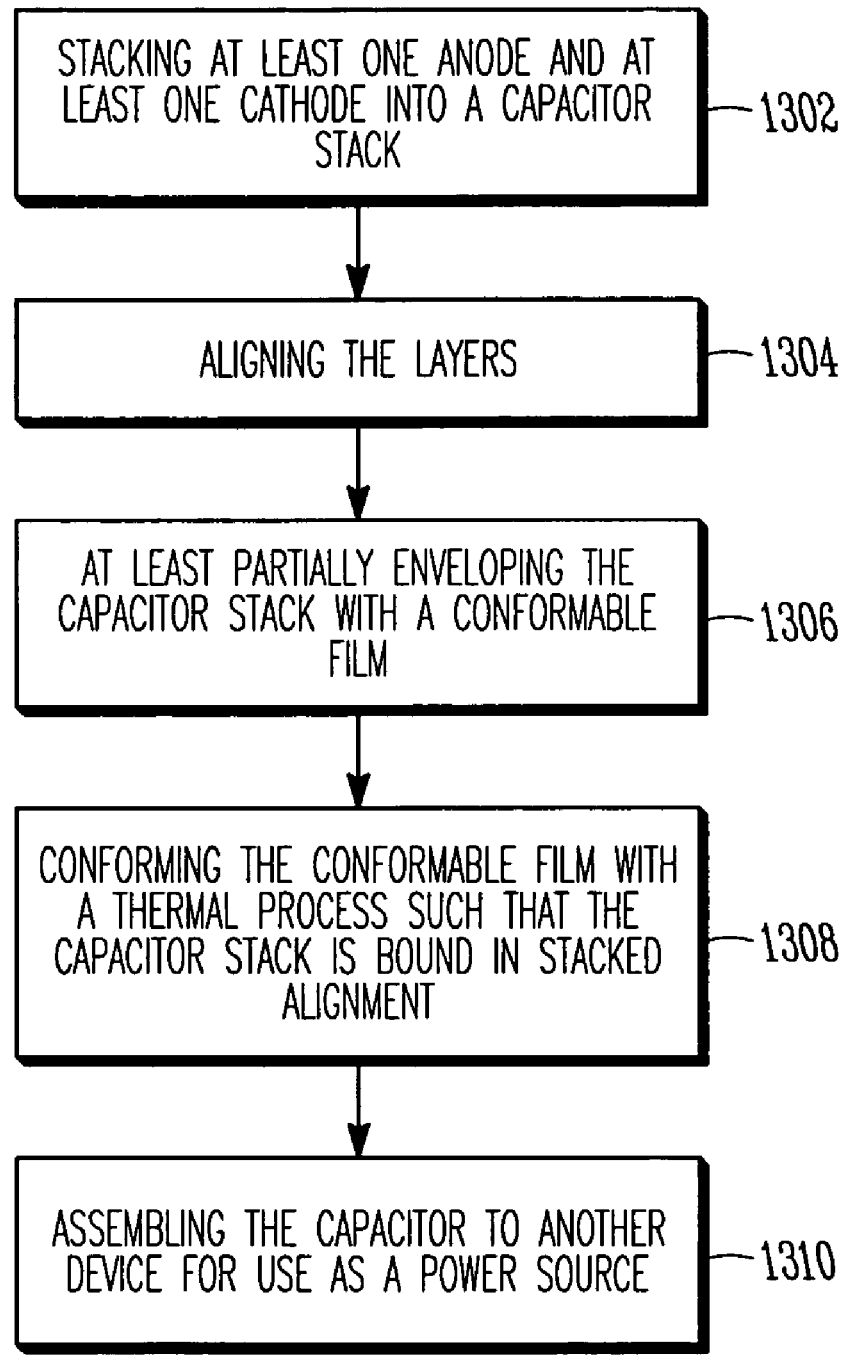
FIG. 13 is a method for making a capacitor stack, according to one embodiment of the present subject matter.

FIG. 13 is a method for making a capacitor stack, according to one embodiment of the present subject matter. The method includes stacking at least one anode and at least one cathode into a capacitor stack 1302. Additionally, the method includes aligning the layers 1304. The method further includes at least partially enveloping the capacitor stack with a conformable film 1306. Also, the method includes conforming the conformable film with a thermal process such that the capacitor stack is bound in stacked alignment 1308. The method additionally includes assembling the capacitor to another device for use as a power source 1310.

Figure 14:
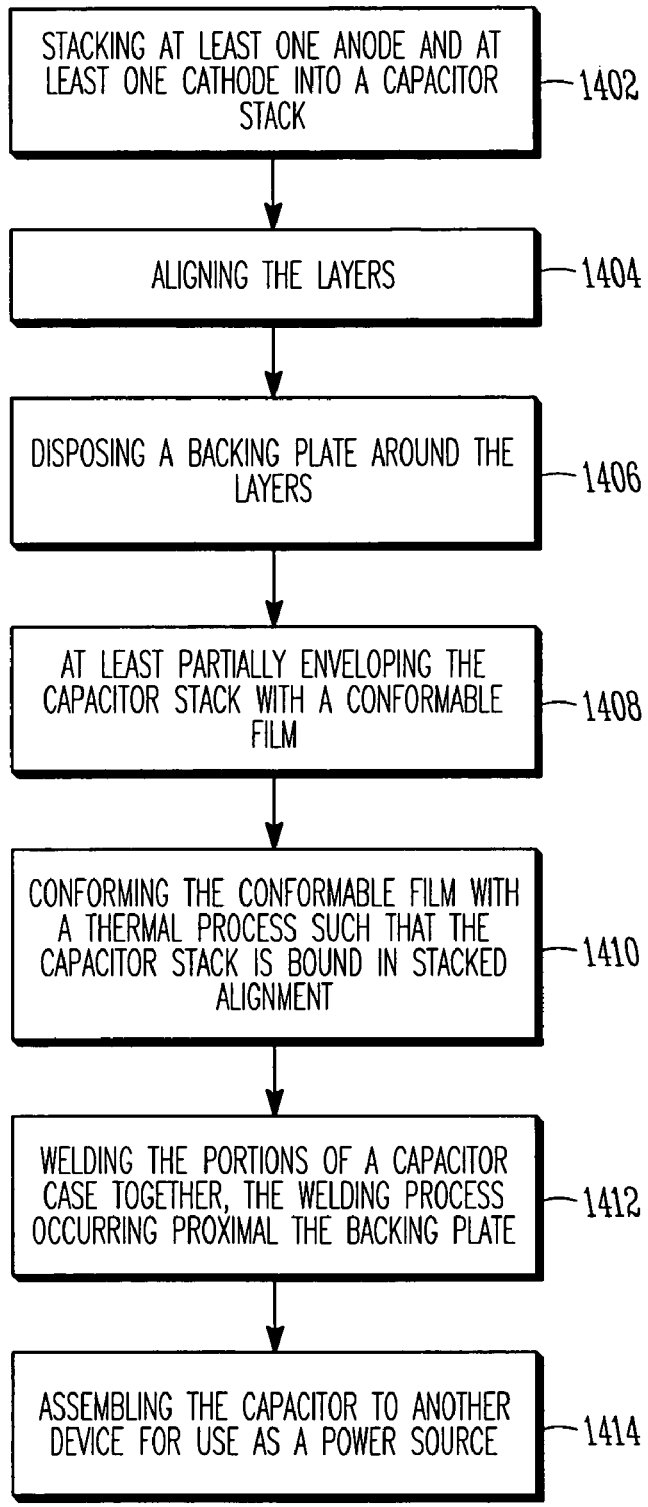
FIG. 14 is a method for making a capacitor stack, according to one embodiment of the present subject matter.

FIG. 14 is a method for making a capacitor stack, according to one embodiment of the present subject matter. The method includes stacking at least one anode and at least one cathode into a capacitor stack 1402. The method further includes aligning the layers 1404. Also, the method includes disposing a backing plate around the layers 1406. The method includes at least partially enveloping the capacitor stack with a conformable film 1408. The method includes conforming the conformable film with a thermal process such that the capacitor stack is bound in stacked alignment 1410. The method, in the embodiment, also includes welding the portions of a capacitor case together, the welding process occurring proximal the backing plate 1412. The method also includes assembling the capacitor to another device for use as a power source 1414.

The methods associated with FIGS. 10-11 are only examples of embodiments within the scope of the present subject matter. Additional combinations of the method steps disclosed also fall within the scope of the present subject matter. Also, additional method features fall within this scope. For example, some methods include at least partially enveloping a forming mandrel with a conformable film, conforming the conformable film to the forming mandrel, and removing the conforming film from the forming mandrel. Some of these embodiments include cutting the conforming film from the forming mandrel. Also, some methods include a thermal process which is a convection process. Some of these methods include convection processes in which air is blown onto the at least one conformable film at a temperature from about 200 degrees Fahrenheit to about 350 degrees Fahrenheit.

Exemplary Embodiment of Implantable Defibrillator

Figure 15:
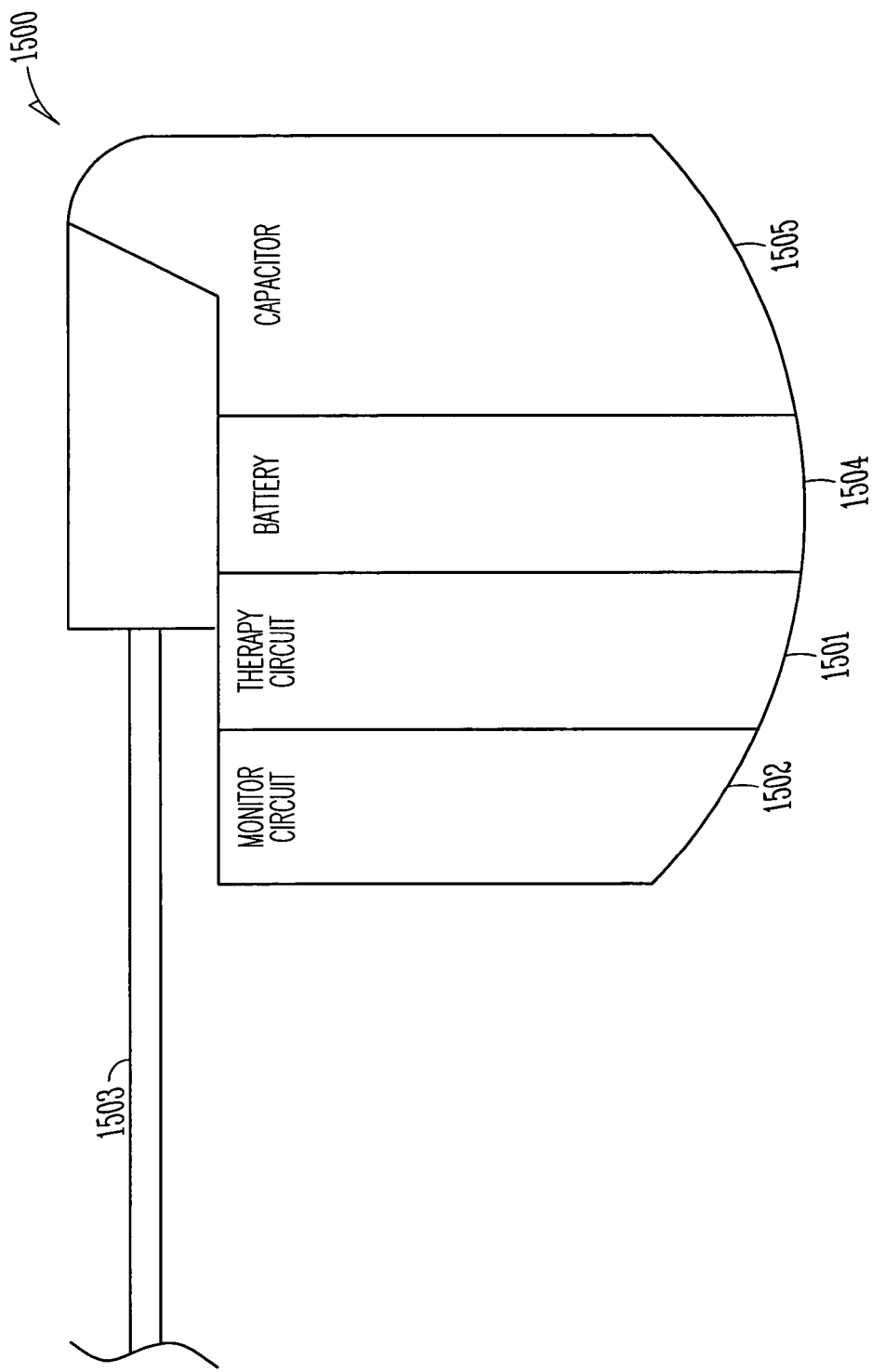
FIG. 15 is a schematic of an implantable device, according to one embodiment of the present subject matter.

FIG. 15 shows one of the many applications for capacitors incorporating one or more teachings of the present subject matter: an implantable heart monitor or apparatus 1500. As used herein, implantable heart monitor includes any implantable device for providing therapeutic stimulus to a heart muscle. Thus, for example, the term includes pacemakers, defibrillators, cardioverters, congestive heart failure devices, and combinations and permutations thereof.

Heart monitor 1500 includes a lead system 1503, which after implantation electrically contact strategic portions of a patient's heart. Shown schematically are portions of monitor 1500 including a monitoring circuit 1502 for monitoring heart activity through one or more of the leads of lead system 1503, and a therapy circuit 1501 for delivering electrical energy through one or more of the leads to a heart. Monitor 1500 also includes an energy storage component, which includes a battery 1504 and incorporates at least one capacitor 1505 having one or more of the features of the exemplary capacitors described above.

In addition to implantable heart monitor and other cardiac rhythm management devices, one or more teachings of the present subject matter can be incorporated into cylindrical capacitors and/or capacitors used for photographic flash equipment. Teachings of the subject matter are pertinent to any application where high-energy, high-voltage, or space-efficient capacitors are desirable. Moreover, one or more teachings are applicable to batteries.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. An apparatus, comprising:
   a capacitor stack, including at least one substantially planar anode layer arranged in stacked alignment adjacent at least one substantially planar cathode layer, with at least one separator layer disposed therebetween;
   a heat shrink film conformed in a continuous band around the capacitor stack;
   a case with a first opening sized for receiving a capacitor stack, the case having at least one feedthrough opening; and
   a lid mateable to the first opening;
   wherein the capacitor stack is disposed in the case, the lid is sealably connected to the first opening, and electrolyte is disposed in the case.

2. The apparatus of claim 1, wherein the conformed heat shrink film includes a seam.

3. The apparatus of claim 1, wherein the conformed heat shrink film includes at least a first piercing, the first piercing adapted for passage of a terminal connected to the capacitor stack.

4. The apparatus of claim 1, wherein the conformed heat shrink film includes at least a first excised opening, the first excised opening for passage of a terminal connected to the capacitor stack.

5. The apparatus of claim 1, wherein the conformed heat shrink film includes a polymeric material.

6. The apparatus of claim 5, wherein the polymeric material includes polyethylene terephthalate.

7. The apparatus of claim 1, wherein the capacitor stack exterior comprises an edge surface extending between a top layer and a bottom layer, the top layer and the bottom layer in substantially parallel alignment, with a perimeter film substantially enveloping the edge surface.

8. An apparatus, comprising:
   a capacitor stack, including at least one substantially planar anode layer arranged in stacked alignment adjacent at least one substantially planar cathode layer, with at least one separator layer disposed therebetween;
   banding means for banding the capacitor stack, the banding means including means that are thermally conformable;

case means for sealably housing the capacitor stack; and electrolyte disposed in the case.

9. The apparatus of claim 8, wherein the capacitor stack defines an exterior having an edge surface extending between a first major planar surface and a second major planar surface, the first major planar surface and the second major planar surface being substantially parallel, wherein the thermally conformed heat shrink means are for substantially enveloping the edge surface.

10. The apparatus of claim 9, wherein the means thermally conformed for enveloping the capacitor stack in a bound state include a perimeter film substantially enveloping the edge surface.

11. The apparatus of claim 8, further comprising a thermoformed means for at least partially enveloping the capacitor stack.

12. The apparatus of claim 8, further comprising a plurality of thermally conformed heat shrink means, each of the plurality of thermally conformed heat shrink for at least partially enveloping the capacitor stack.

13. The apparatus of claim 8, wherein the thermally conformed heat shrink means include a polymeric material.

14. The apparatus of claim 13, wherein the polymeric material includes polyethylene terephthalate.

15. The apparatus of claim 8, wherein the thermally conformed heat shrink means includes a perimeter film.

16. An apparatus, comprising:
a capacitor stack, including at least one substantially planar anode layer arranged in stacked alignment adjacent at least one substantially planar cathode layer, with at least one separator layer disposed therebetween;
a heat shrink film conformed in a continuous band around the capacitor stack;
a case, with the capacitor stack sealably disposed in the case such that an anode terminal extending through the case is electrically coupled with the at least one substantially planar anode layer, and a cathode terminal is electrically coupled with at least one substantially planar cathode layer;
electrolyte disposed in the case;
pulse generation electronics electrically coupled to the anode terminal and the cathode terminal;
at least one battery coupled to the pulse generation electronics and the capacitor stack;
an implantable can, in which the case, the pulse generation electronics, and the battery are disposed; and
a feedthrough coupled to the can and including at least one terminal electrically coupled to the pulse generation electronics.

17. The apparatus of claim 16, wherein the pulse generation electronics include defibrillation electronics.

18. The apparatus of claim 16, wherein the conformed heat shrink film including polyethylene terephthalate.

19. The apparatus of claim 16, wherein the conformed heat shrink film is electrically insulative and is disposed between the at least one substantially planar anode layer and the case.

20. The apparatus of claim 16, wherein the conformed heat shrink film is seamless.

* * * * *